United States Patent [19]

Gillespie et al.

[11] Patent Number: 4,741,202

[45] Date of Patent: * May 3, 1988

[54] MOISTURE VAPOR TRANSMISSION TEST CELL

[75] Inventors: Ronald J. Gillespie, Milltown; Allan P. Farrington, Englishtown, both of N.J.

[73] Assignee: Johnson & Johnson, New Brunswick, N.J.

[*] Notice: The portion of the term of this patent subsequent to Apr. 15, 2003 has been disclaimed.

[21] Appl. No.: 850,798

[22] Filed: Apr. 11, 1986

Related U.S. Application Data

[63] Continuation-in-part of Ser. No. 722,931, Apr. 12, 1985, Pat. No. 4,581,921.

[51] Int. Cl.$^4$ ............................................. G01N 5/02
[52] U.S. Cl. ............................................. 73/73; 73/38
[58] Field of Search ............................ 73/73, 38, 76

[56] References Cited

U.S. PATENT DOCUMENTS

2,080,168  5/1937  Dietert .................................. 73/76
4,581,921  4/1986  Gillespie et al. ..................... 73/73

Primary Examiner—William A. Cuchlinski, Jr.
Assistant Examiner—W. Morris Worth
Attorney, Agent, or Firm—Lawrence D. Schuler

[57] ABSTRACT

A test cell comprises a first enclosure which is closed at one end and open at the other. A fan is located near the closed end for supplying conditioned air to the first enclosure and an aperture in the bottom wall of the enclosure near its open end. An apertured sample holder may be used to hold the test specimen in place during use. The first enclosure is preferably divided into first and second compartments by a slotted divider. The test cell may optionally include a baffle near its closed end to reduce eddying of the air and to provide a uniform air flow pattern across the test specimen. The test cell of the present invention may be used in conjunction with the apparatus described in U.S. Pat. No. 4,357,827 to measure moisture vapor transmission characteristics of a test specimen.

7 Claims, 5 Drawing Sheets

MOISTURE VAPOR TRANSMISSION TEST CELL

This is a continuation-in-part of our copending patent application Ser. No. 722,931, filed Apr. 12, 1985 now U.S. Pat. No. 4,581,921.

The invention relates to a test cell and more particularly to a test cell which may be used to determine the moisture vapor transmission characteristics of a test specimen, such as a nonwoven fabric, a plastic film or the like.

BACKGROUND OF THE INVENTION

U.S. Pat. No. 4,357,827 to McConnell describes an apparatus for determining the weight of liquid flowing to or from a test site. The McConnell apparatus comprises a vessel 12 for containing a liquid to be used in testing the performance of a sample 30. Vessel 12, which is supported by a balance 16, includes a siphon tube 22 which is connected to the bottom of a test cell 26 by tubing 24. Test cell 26, which has an upper surface 28 on which the test specimen is placed, is mounted on an O-shaped support 32. As exemplified in FIGS. 1 and 2 of U.S. Pat. No. 4,357,827, test cell 26 is a flat disk-shaped plate having a hole 56 in the center through which liquid can flow to the test specimen via tubing 24. Each of the test cells 26, 60 and 66 illustrated in U.S. Pat. No. 4,357,827 is provided with a flange 58 so that the cell will fit into the aforementioned ring-shaped support 32.

SUMMARY OF THE INVENTION

In accordance with the present invention, there is provided a test cell which can be used in conjunction with the apparatus described in U.S. Pat. No. 4,357,827 to determine the moisture vapor transmission characteristics of a test specimen such as a nonwoven fabric or a plastic film.

The test cell of the present invention comprises a first enclosure having a top wall, a bottom wall, and a pair of opposed side walls. This enclosure is closed at one end and open at its other end.

Means are provided near the closed end of the first enclosure for supplying conditioned air to the test cell. There is an aperture, circular in configuration, in the bottom wall of the first enclosure near its open end. A second enclosure defined by a peripheral wall and a bottom wall, is detachably secured to the lower surface of the bottom wall of the first enclosure near the open end thereof so as to be in fluid communication with the first enclosure. The interior of the second enclosure is circular in cross-section. The bottom wall of the second enclosure comprises an inlet through which a test liquid, such as water, may be admitted to an interiorly located reservoir which is covered with a porous plate. The thickness of this porous plate is such that when the second enclosure is attached to the lower surface of the bottom wall of the first enclosure, the upper surface of the porous plate is located in a plane which is below the plane in which the upper surface of the bottom wall of the first enclosure is located. Thus, when a test specimen is positioned on the upper surface of the bottom wall of the first enclosure to cover the aforementioned aperture, a head space is left between the lower surface of the positioned test specimen and the upper surface of the porous plate. As will be seen later herein, when the test cell is in use this head space will contain the vapor of a test liquid which has been supplied to the porous plate.

In a preferred embodiment, the first enclosure includes a slotted divider which divides the first enclosure into a first compartment located adjacent the closed end of the first enclosure and a second compartment located adjacent the open end of the first enclosure. In the preferred embodiment, as will be seen, the aforementioned means for supplying conditioned air is associated with the first compartment, while the aforementioned aperture in the first enclosure is located in the bottom wall of the second compartment. In the preferred embodiment, the means for supplying conditioned air to the test cell comprises a fan mounted at the top of a hollow riser which is located on the top wall of the first compartment so as to be in fluid communication therewith. A baffle may be optionally located in the first compartment to minimize eddying of the conditioned air and provide a uniform profile as the air flows across the test specimen.

In a modification of the present invention, there is provided a test cell which comprises the aforementioned first enclosure and means for supplying air to that enclosure but which does not, however, include the aforementioned second enclosure, porous plate or means for conducting a test liquid to the interior of the second enclosure. This modified test cell may be used, as will be explained hereinafter, to estimate the amount of and rate at which moisture vapor passes through a material to be tested. Although the results obtained by use of this modified test cell are less accurate than those obtained with the test cell first described above, the modified test cell is quite useful for initially screening various materials for their vapor transmission characteristics.

DETAILED DESCRIPTION OF THE INVENTION

Figure 2:
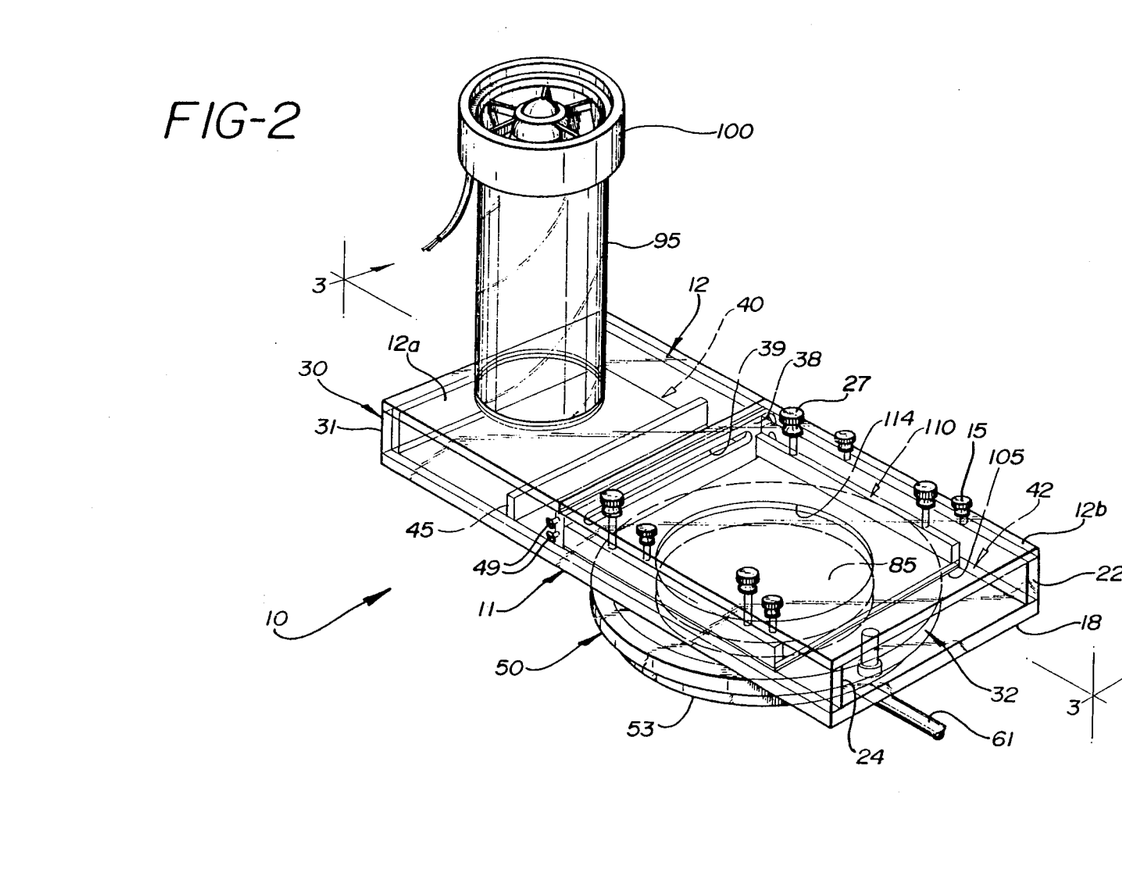
FIG. 2 is a perspective view of the test cell of the invention.
Figure 3:
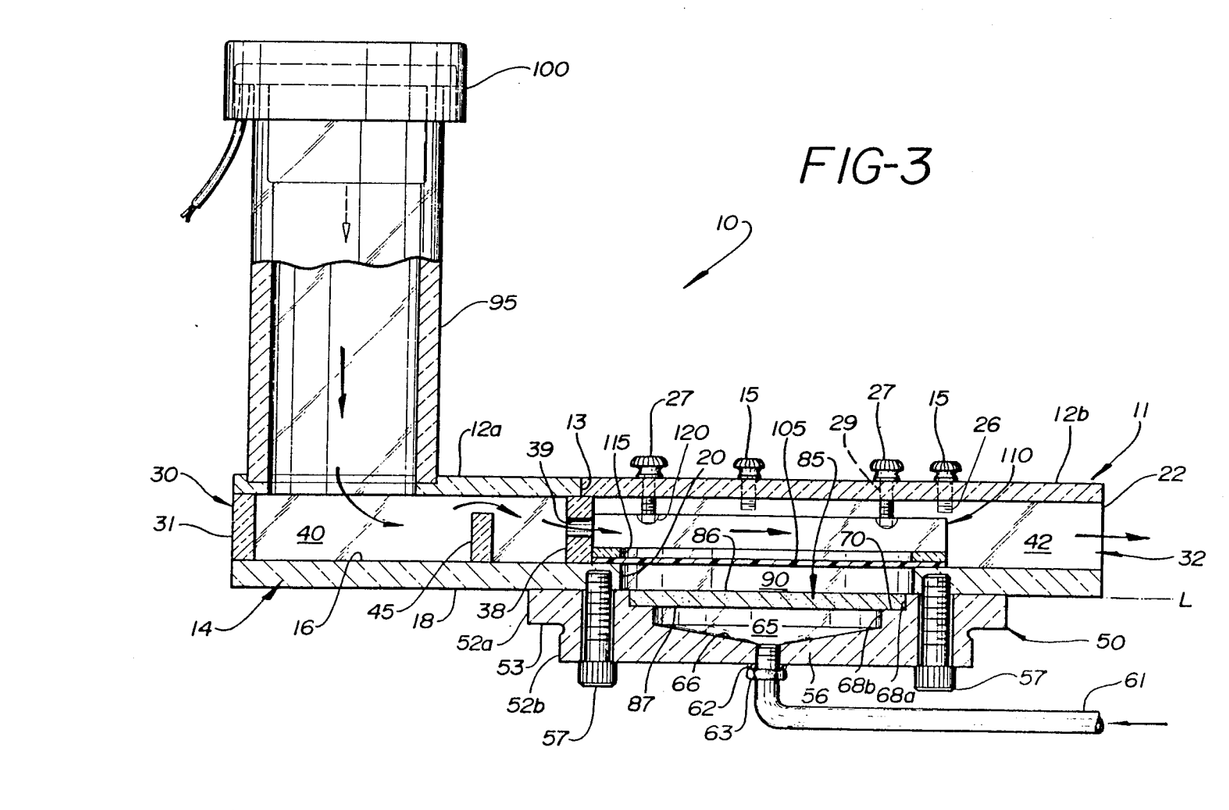
FIG. 3 is a cross-sectional view taken along line 3—3 of FIG. 2.
Figure 4:
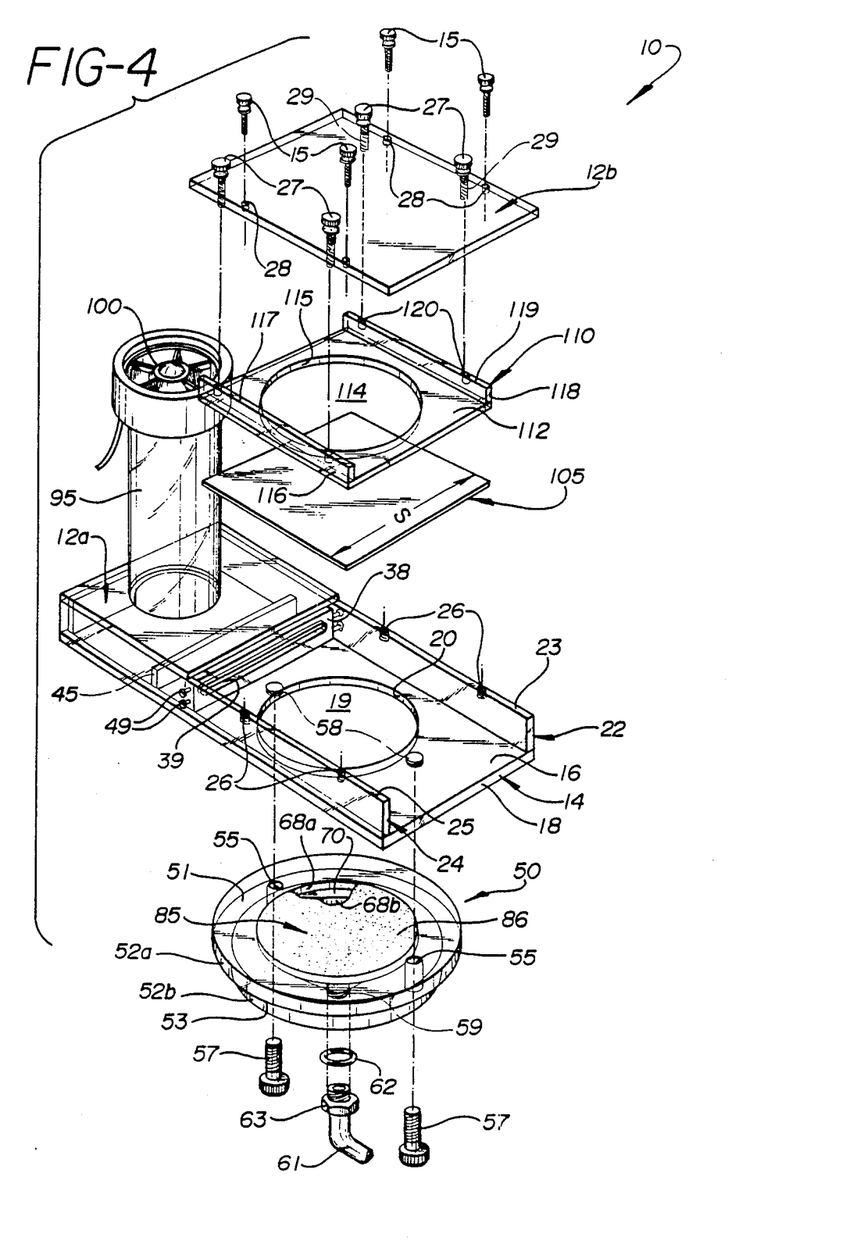
FIG. 4 is an exploded perspective of the test cell and sample to be tested.

Referring now to the drawings, and especially to FIGS. 2-4, test cell 10 in accordance with the present invention comprises a first enclosure 11, a second hollow enclosure 50, and means 100 for circulating a gas, such as air through the device.

First enclosure 11 comprises a top wall 12, a bottom wall 14, a first side wall 22 and a second side wall 24. The first end 30 of the enclosure 11 is closed by an end wall 31; the second end 32 of the enclosure is open. Bottom wall 14 has an upper surface 16 facing interiorly of enclosure 11 and a lower surface 18 facing exteriorly of the enclosure.

First enclosure 11 is divided into a first compartment 40 and a second compartment 42 by an interiorly located divider 38 which extends laterally from first side wall 22 to second side wall 24 and vertically from top wall 12 to bottom wall 14. Divider 38 includes a laterally extending elongated slot 39 for establishing fluid communication between the first and second compartments. Slot 39 is preferably located midway between the upper and lower edges of divider 38. As can best be seen in FIG. 4, the portion of bottom wall 14 which is associated with the second compartment includes a circular aperture 19 defined by an interiorly located circular wall 20.

Top wall 12 comprises a first portion 12a located nearer end 30 of the test cell and a detachably securable second portion 12b located nearer open end 32. As illustrated in FIG. 3, the inwardly disposed ends of the first and second portions of the top wall abut each other, when the test cell is assembled for use, along a line 13 located centrally of the top edge of divider 38 and extending between side walls 22 and 24. When the test cell is in use, top wall portion 12b is held in place by screws 15 which pass through receiving holes 28 drilled into wall portion 12b and are threaded into threaded holes 26 in the upper edges 23 and 25, respectively, of side walls 22 and 24. Upper wall portion 12b also includes four threaded holes 29 into which screws 27 are threaded. The purpose of screws 27 will be explained hereinafter.

Second enclosure 50, which is generally circular in plan view, comprises a perimetric wall and a bottom wall 56. As best seen in FIG. 3, the perimetric wall has an upper portion 52a and a lower portion 52b. Upper portion 52a has a larger diameter than that of lower portion 52b so that second enclosure 50 is provided with an annular flange having a lower surface 53. Referring to FIG. 4, the perimetric wall of enclosure 50 has a pair of diametrically opposed holes 55, 55 drilled therethrough for receiving screws 57 which are threaded into threaded holes 58 provided in lower surface 18 of bottom wall 14. Thus, second enclosure 50 may be detachably secured to the lower surface of first enclosure 11 in the region surrounding aperture 19.

Bottom wall 56 of the second enclosure has a centrally disposed interiorly threaded aperture 59 for receiving an externally threaded, continuously hollow L-shaped inlet fitting 61 which can be made from metal or plastic. When inlet 61 is screwed into aperture 59 in bottom wall 56, means are provided whereby a test liquid such as water may be introduced into or withdrawn from the interior of second enclosure 50. An O-ring 62 placed over the threaded portion of inlet fitting 61 to rest against the upper surface of flange 63 provides a fluid tight seal.

Enclosure 50 further includes an interiorly located region defined by a sloped interiorly located bottom wall 66 and an interiorly located side wall having an upper portion 68a and a lower portion 68b. As can be seen in FIG. 3, the diameter of lower portion 68b of the interiorly located side wall corresponds to the diameter of bottom wall 66. The diameter of upper portion 68a of the interiorly located side wall is larger than that of lower portion 68b so that there is provided an interiorly located circular ledge 70 on which rests a porous plate 85 which has an upper surface 86 and a lower surface 87. In the specific embodiment under discussion, the diameter of upper wall portion 68a is somewhat smaller than the diameter of opening 19 in bottom wall 14.

Test cell 10 further comprises a hollow cylindrical riser 95 which is in fluid communication, via an aperture in top wall portion 12a, with first compartment 40. A fan 100, which may be AC or DC powered, is secured in place at the upper end of riser 95. The fan and riser cooperate to provide means for circulating a gas, such as air, through the test cell.

Referring to FIG. 4, numeral 105 designates a specimen, e.g. a nonwoven fabric or a plastic film, which is to be mounted in the test cell for testing. Specimen 105, which will overlie aperture 19 when positioned for testing, is conveniently in the shape of a square and is cut so that the length, s, of its sides is somewhat greater than the diameter of aperture 19 in bottom wall 14 of compartment 42. It is preferable to provide a sample retaining device to keep the test specimen in place during the test procedure. Retainer 110 comprises a base plate 112 whose width is somewhat less than the distance between side walls 22 and 24 and whose length is somewhat larger than the diameter of aperture 19. Base plate 112 includes a circular opening 114 which is defined by interiorly located wall 115 and whose diameter is preferably substantially equivalent to the diameter of aperture 19 in bottom wall 14. Base plate 112 also includes a pair of opposed upstanding rails 116, 118 whose height is somewhat less than the distance between the inner surfaces of top and bottom walls, 12 and 14, respectively. The upper surfaces 117 and 119, respectively, of rails 116 and 118 may, if desired, be provided with a pair of circular depressions 120. In use, test specimen 105 is mounted so as to cover aperture 19 in the bottom of second compartment 42. Retainer 110 is then placed over specimen 105 so that rails 117, 119 are disposed upwardly as the reader views FIG. 4. Top wall portion 12b is then put into position overlying compartment 42. Screws 15 are inserted into receiving holes 28 and turned into threaded openings 26 in upper surfaces 23 and 25 of side walls 22 and 24. Screws 27 in top wall portion 12b are inserted into threaded receiving holes 29 and then turned so that their respective ends come into contact with depressions 120. This positioning of the ends of screws 27 in depressions 120 urges retainer 110 toward the bottom wall of compartment 42, thus effectively securing test specimen 105 between the lower surface of base plate 112 and the upper surface 16 of bottom wall 14. It also ensures that opening 114 in base plate 112 is concentrically aligned with aperture 19 in bottom wall 14.

Porous plate 85, which may be made of fritted glass or other suitable material, has pores whose sizes are sufficient to allow the passage of water or other test liquid therethrough. The thickness of porous plate 85 is preferably made equal to the depth of interior side wall 68a so that upper surface 86 of the porous plate is in the same plane in which the upper surface 51 of second enclosure 50 contacts lower surface 18 of wall 14 of the first enclosure. This arrangement provides a reservoir 65 for a pool of test liquid beneath porous plate 85, said reservoir being defined by the lower surface 87 of the porous plate, interiorly located side wall portion 68b, and interiorly located bottom wall 66. When porous plate 85 is sized in the manner just described there is formed a circular head space 90 between upper surface 86 of the porous plate and the lower surface of test specimen 105, the depth of this head space corresponding to the height of circular side wall 20 which defines aperture 19 in bottom wall 14. If desired, the thickness of porous plate 85 may be made lesser than or greater than the vertical height of interior wall portion 68a; in all cases, however, a head space 90 must be left between the upper surface of the porous plate and the lower surface of the positioned test specimen. At equilibrium conditions during testing, head space 90 contains the vapor of the test liquid which is supplied to the device through inlet fitting 61.

Test cell 10 may optionally include a baffle 45 which is secured in first compartment 40. Baffle 45 may be about three-sixteenths inch thick. It extends laterally of the device from side wall 22 to side wall 24 in the same manner as divider 38. As will be seen in FIG. 3, however, baffle 45 does not extend vertically to top wall 12, that is, the height of baffle 45 is less than the distance between the interior surfaces of bottom wall 14 and top wall 12. Air passing down riser 95 and through compartment 40 must pass over the upper edge of baffle 45. As mentioned earlier, this baffle reduces eddying of the air as it flows through slot 39 and provides a uniform profile as the air flows across the test specimen in second compartment 42.

Figure 1:
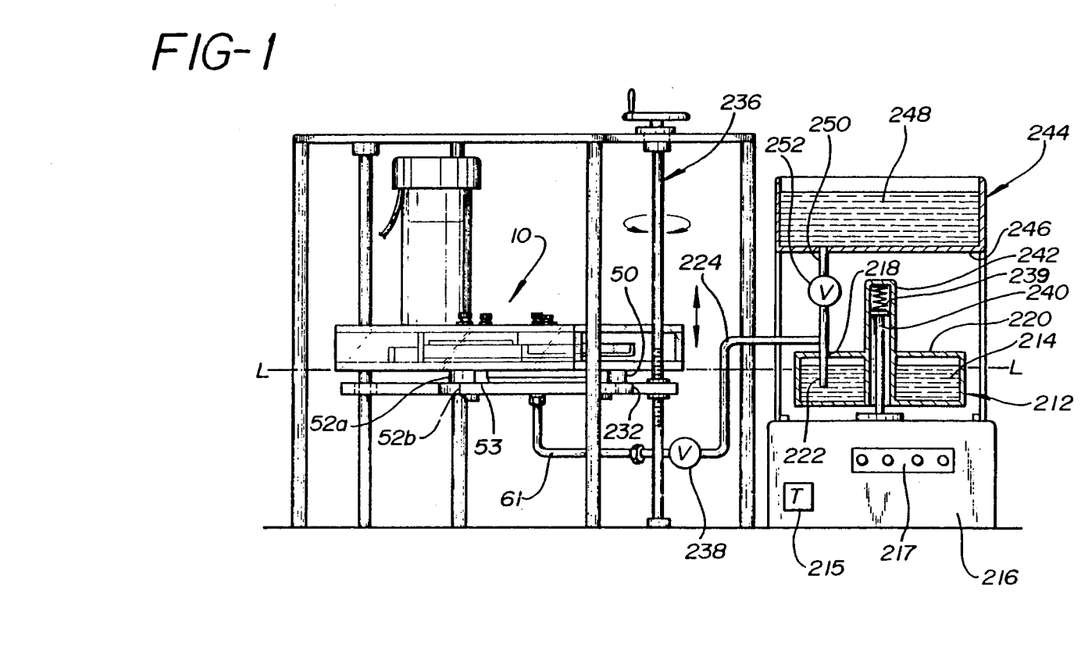
FIG. 1 is a schematic of a test apparatus employing the test cell of the present invention.

The test cell of the present invention may be used in conjunction with the apparatus disclosed in U.S. Pat. No. 4,357,827, the teachings of which are incorporated herein by reference, in order to determine the amount of and rate at which the vapor of a test liquid is transmitted through a given material such as a nonwoven fabric or a plastic film. FIG. 1 shows the test apparatus of U.S. Pat. No. 4,357,827 on which has been mounted test cell 10 of the present invention. In FIG. 1, at the right hand side, there is shown vessel 212 which is a reservoir for a liquid 214, such as water, to be employed in testing a test specimen 105. Vessel 212, which is supported by the weight sensing surface of a weighing means such as an electronic balance 216 having a tare switch 215 and a display 217, is preferably closed and includes a hole 218 in its top 220 through which a siphon tube 222 may be lowered. A test liquid (water is used when moisture vapor transmission (MVT) is to be determined) is introduced into vessel 212 to a predetermined level "L". Siphon tube 222 is inserted through hole 218 so that it extends down into test liquid 214. Siphon tube 222 is connected via tubing 224 to inlet tubing 61 of test cell 10. As seen in FIG. 1, test cell 10 of the present invention is mounted so that the lower surface 53 of the flange provided by upper wall portion 52a rests on O-shaped support 232 of the test apparatus.

In order to adjust the vertical position of test cell 10, O-shaped support 232 on which the test cell is mounted is attached to an adjustable jack 236. A hydrostatic head of zero may then be achieved between the reservoir of liquid 214 and the upper surface 86 of porous plate 85 by maintaining said upper surface 86 in the same horizontal plane, "L", as the upper surface of liquid 214 is vessel 212. Jack 236 permits an operator to adjust the vertical position of the upper surface 86 of porous plate 85 in order to obtain a desired hydrostatic head.

As disclosed in U.S. Pat. No. 4,357,827, vessel 212 is mounted on balance 216 by means of a leveling spring 239 and a mounting pin 240. Mounting pin 240 on the balance is adapted to fit into a mounting tube 242 in the center of vessel 212. Mounting tube 242 contains spring 239 which, when vessel 212 is in place of the mounting pin 240, is compressed between the top of pin 240 and the top of mounting tube 242. The compression strength of spring 239 is selected so that vessel 212 will remain at a constant elevation as test liquid 214 flows into or out of it. As is further disclosed in U.S. Pat. No. 4,357,827, the test apparatus of McConnell preferably comprises a reserve tank 244 that is constructed to fit over vessel 212, but without touching vessel 212 and without impinging on the weight sensing surface of balance 216. Reserve tank 244 contains a reserve compartment 246 for containing a reserve quantity 248 of the test liquid. Reserve compartment has an outflow conduit 250 through which the reserve quantity of liquid may flow into vessel 212. An outflow valve 252 in conduit 250 controls the flow of liquid.

The amount of and rate at which moisture vapor passes through a given material may be determined as follows. The material to be tested is cut into a square shaped test specimen 105 sufficient in size to cover aperture 19. The test specimen is then weighed and its initial weight, $W_i$, is recorded. Specimen 105 is then placed over aperture 19 where it is held in place by sample holder 110. Top wall portion 12b is then put into position. Screws 15 are passed through receiving holes 28 and threaded into threaded openings 26 to thereby keep top wall portion 12b securely in place. Screws 27 are then turned down through threaded holes 29 so as to engage circular depressions 120 to thereby keep sample holder 110 and test specimen 105 in proper position. This also serves to seal the outer edges of the lower surface of test specimen 105 against upper surface 16 of bottom wall 14 in the region surrounding aperture 19 thus ensuring that the moisture vapor in head space 90 will be transmitted, if at all, through the material being tested.

Water is added to reservoir 214 and is conducted through siphon tube 222, tubing 224, on-off valve 238 and inlet fitting 61 on test cell 10 into reservoir 65. Test cell 10 is adjusted vertically so as to bring upper surface 86 of porous plate 85 slightly (e.g. 3 mm) above the horizontal plane of the upper surface of the water in reservoir 212. This vertical adjustment causes water to flow through the pores of the porous plate toward its upper surface 86 where the water is then free to evaporate into head space 90.

The room in which the testing apparatus is located is maintained at a pre-selected constant temperature and constant humidity (e.g., 50% relative humidity and 72° F.). Air at the selected temperature and humidity conditions is circulated through test cell 10 by fan 100. The air passes downwardly through riser 95, over the top edge of baffle 45, through slot 39 is divider wall 38, across the top of test specimen 105, and out the open end 32 of the test cell. As water evaporates from the upper surface of porous plate 85 and passes through test specimen 105, it is replenished from vessel 212. At the end of the test cycle, balance 216 indicates the weight, $W_o$, of water which has flowed out of reservoir 212 into the test cell.

In order to determine the weight, $W_t$, of water vapor which has actually been transmitted through test specimen 105, it is necessary to correct the quantity $W_o$ to account for (1) the weight, $W_r$, of water retained by the test specimen during the course of the test cycle and (2) the weight, $W_e$, of water which has evaporated into the atmosphere from the surface of the water in reservoir 212 (such evaporation can occur, for example, through hole 218 in the top of the reservoir).

$W_r$ is determined as follows. At the end of the test cycle (which can be, e.g., one hour or any other desired time), the test specimen is removed from the test cell and its final weight, $W_f$, is determined. $W_r$ is then determined by subtracting the initial weight, $W_i$, of the test specimen from the final weight, $W_f$, of the test specimen.

The weight, $W_e$, of water which has evaporated from reservoir 212 may be determined by replacing the test specimen with a piece of water-impervious material (e.g., a sheet of solid plastic) and repeating the test cycle for an identical time period. Balance 216 will then give a direct readout of the weight, $W_e$, which evaporated from reservoir 212 during the test cycle.

The weight of water vapor, $W_t$, transmitted through test specimen 105 during the test cycle is then determined from the following equation:

$$W_t = W_o - W_r - W_e \qquad [1]$$

or $$W_t = W_o - (W_f - W_i) - W_e \qquad [2]$$

The moisture vapor transmission rate of the material under test can then be readily calculated from the amount of water vapor, $W_t$, which has been determined to have been transmitted through the test specimen, the length of time over which the test was conducted, and the area of the test specimen which was exposed to the moisture vapor at aperture 19.

Test cell 10, except for fan means 100, porous plate 85 and O-ring 62, was constructed of synthetic resin materials. Other materials of construction may be used if desired. The first enclosure 11 was made of 3/16 inch (0.48 cm) sheets of polymethyl methacrylate. The various pieces were sealed together by the use of a methylene chloride/acetone solution. Screws 49 were used to hold divider 38 securely in place. Screws 15, 27 and 49 were made of nylon. Riser 95, whose height to inside diameter ratio was approximately 2.5:1, was cut from a 3/16 inch thick (0.48 cm) piece of polymethyl methacrylate tubing having an inside diameter of about 2 inches. Second enclosure 50 was machined from a solid block of the methacrylate resin, the diameter of wall portion 52a was about 6 inches (15.2 cm), while the diameter of wall portion 52b was about 5¼ inches (13.3 cm). Aperture 19 was about 3¾ inches (9.5 cm) in diameter. Porous plate 85 comprised a fritted glass disc having continuous pores so that a test liquid, such as water, could readily flow therethrough. The porous plate was about 3½ inches (8.9 cm) in diameter and about ¼ inch (0.63 cm) thick. The diameter of wall portion 68a was somewhat larger than the diameter of the porous plate, and its height was substantially the same as the thickness of porous plate 85. The diameter of wall portion 68b was approximately 2⅞ inches (7.3 cm) in diameter; its height was about 3/16 inch (0.48 cm). Sample holder 110 was in the form of a square the length of whose side was about 4.5 inches (11.4 cm). Opening 114 had a diameter of about 3¾ inches (9.5 cm) in outside dimension. Enclosure 11 was about 11 inches (28 cm) long, 5 inches (12.7 cm) wide and about 1 5/16 inches (3.3 cm) high. Divider 38 was located about 4 inches (10.2 cm) from the inner surface of end wall 30. Baffle 45 was located about 3¾ inches (9.5 cm) from the inner surface of end wall 30. Slot 39 was about 4 inches (10.2 cm) long and 3/16 inch (0.48 cm) high. Fan means 100 was an Aximax 2 d.c. fan, Model No. 606NS-026958, purchased from Rotron, Inc.

Following the procedure explained earlier, the test cell was used to determine moisture vapor transmission rate (MVTR) of a non-woven fabric used as a facing in a commercially available baby diaper, a piece of Celgard® microporous film and a piece of men's shirting fabric (80% polyester/20% cotton blend). Results were as follows (50% relative humidity, 72° F. constant temperature):

| Material | MVTR |
|---|---|
| Non-woven Fabric | 83.78 gm./hr. $-M^2$ |
| Microporous film | 74.01 gm./hr. $-M^2$ |
| Shirting fabric | 79.59 gm./hr. $-M^2$ |

Figure 5:
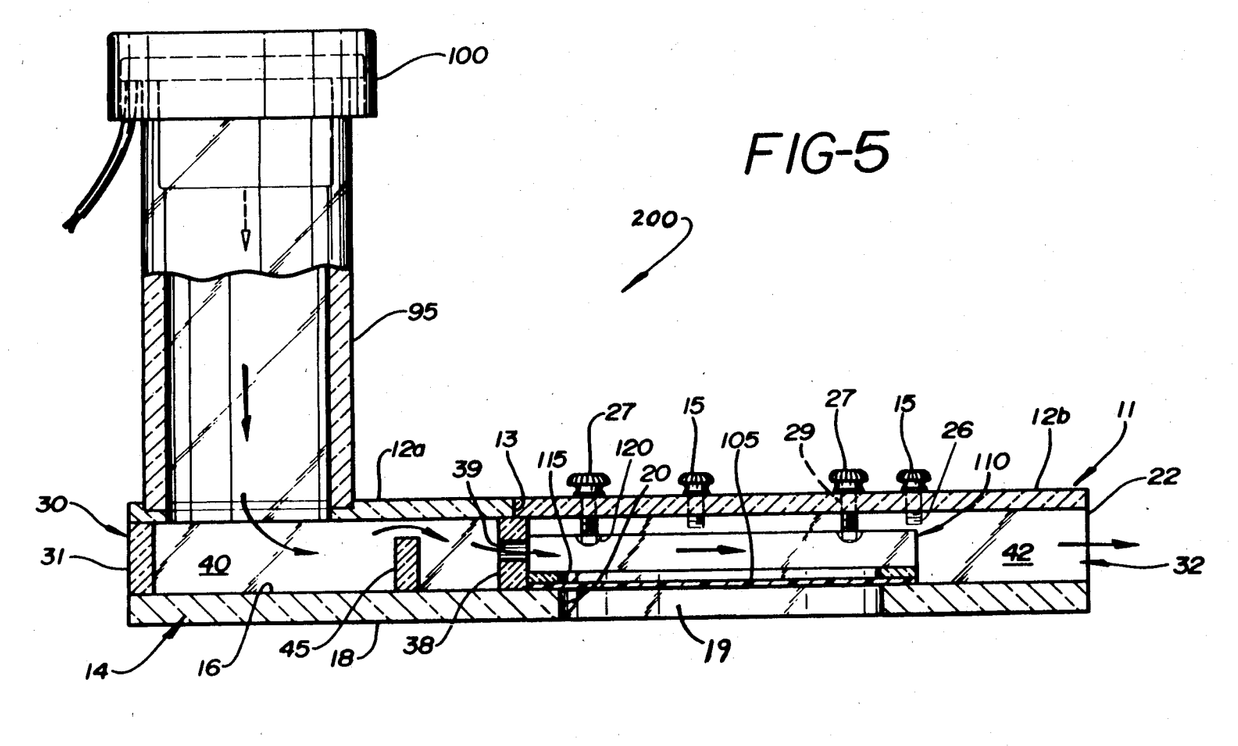
FIG. 5 is a cross-sectional view showing a second embodiment of the test cell of the present invention.

Referring now to FIG. 5, there is shown another embodiment of a test cell in accordance with the present invention. Test cell 200 comprises an enclosure 11 which is identical to that described earlier herein in connection with test cell 10. It also includes means, i.e. riser 95 and fan 100, for circulating a gas such as air through the test cell. It will be understood that structural components of the modified test cell 200 in FIG. 5 which are identical to structural parts of test cell 10 in FIGS. 1–4 are identified by the same reference numerals. The modified test cell preferably includes slotted divider 38 and/or baffle 45. The bottom wall 14 of test cell 200 includes, near its open end, an aperture 19 defined by an interiorly located circular wall 20.

Test cell 200 may be used with an ordinary laboratory Petri dish to estimate moisture vapor transmission characteristics of a particular sample. Test specimen 105 is first weighed and then mounted over aperture 19 of the modified test cell in the manner described earlier. A Petri dish whose outside diameter is somewhat less than the diameter of aperture 19 is filled with a test fluid, e.g. water, and the total weight of dish and water is determined. Modified test cell 200 with the test specimen mounted therein is then placed over the Petri dish so that the dish is located within aperture 19 in the lower wall of enclosure 11. This provides a reservoir of test fluid below the lower surface of test specimen 105. At periodic time intervals, the modified test cell is carefully removed, the Petri dish and test fluid are weighed, and the amount of test fluid lost from the Petri dish is determined. The amount of test fluid lost from the Petri dish corresponds approximately to the amount of test fluid which has passed through the test specimen. The approximate rate at which test fluid passes through the specimen under test can be calculated by dividing the weight of water lost from the Petri dish by the time elapsed since the start of the test procedure. It will be recognized that in conducting tests with the modified test cell, the Petri dish and the modified test cell should be put on a smooth, flat surface so as to minimize the amount of test fluid which may be lost without actually passing through the test specimen. Additionally, it will be recognized that the time taken for the periodic weighing of the Petri dish and test fluid should be kept at a minimum in order to obtain reasonably accurate estimates of vapor transmission characteristics.

What is claimed is:
1. A test cell useful in determining moisture vapor transmission characteristics comprising:
   an enclosure having
      a top wall,
      a bottom wall having an upper surface and a lower surface,
      a first side wall,
      a second side wall,
      a first end which is closed by an end wall, and a second end which is open;
   means associated with said enclosure near its first end for supplying air to said enclosure, and
   an aperture in the bottom wall of said enclosure near its open end.

2. A test cell according to claim 1 wherein a portion of the top wall of said enclosure is detachably securable.

3. A test cell according to claim 1 wherein said enclosure further includes a slotted divider which divides said enclosure into a first compartment located between said end wall and said divider and a second compartment located between said divider and said open end.

4. A test cell according to claim 3 wherein said means for supplying air to said enclosure comprises a fan means mounted on a hollow riser which is mounted on the top wall of said first compartment and is in fluid communication with said first compartment.

5. A test cell according to claim 3 wherein the aperture in the bottom wall of said enclosure is located in said second compartment.

6. A test cell according to claim 3 wherein said first compartment includes a baffle spaced from said slotted divider.

7. A test cell according to claim 3 wherein said means for supplying air to said enclosure comprises a fan means mounted on a hollow riser which is mounted on the top wall of said first compartment and is in fluid communication with said first compartment, said aperture in the bottom wall of said enclosure is located in said second compartment, and said first compartment includes a baffle spaced from said slotted divider.

* * * * *